US00PP25097P3

(12) United States Plant Patent
Dobres

(10) Patent No.: US PP25,097 P3
(45) Date of Patent: Nov. 25, 2014

(54) ***CARYOPTERIS* PLANT NAMED 'NOVACARYFOU'**

(50) Latin Name: *Caryopteris hybrida*
Varietal Denomination: Novacaryfou

(71) Applicant: NovaFlora LLC, West Grove, PA (US)

(72) Inventor: Michael S. Dobres, Philadelphia, PA (US)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 13/694,072

(22) Filed: Oct. 26, 2012

(65) Prior Publication Data

US 2014/0123355 P1 May 1, 2014

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Kent L Bell
(74) *Attorney, Agent, or Firm* — Buchanan Ingersoll & Rooney, PC

(57) ABSTRACT

A new and distinct *Caryopteris* plant is provided which is the product of a controlled breeding program followed by selection. Large vibrant violet-blue flowers in a verticillaster arrangement are formed on a substantially uniform basis. The growth habit is rounded ascending with strong branching. Attractive large glossy dark green foliage is formed. The plant is well suited for providing attractive colorful ornamentation in the landscape.

1 Drawing Sheet

Botanical/commercial classification: *Caryopteris hybrida*/ Blue Mist Shrub.

Varietal denomination cv. Novacaryfou.

SUMMARY OF THE INVENTION

*Caryopteris* plants commonly are recognized to be a member of the Laminaceae family and are sometimes identified by the Blue Mist and Bluebeard common names.

A new *Caryopteris hybrida* plant of the present invention was formed at West Grove, Pa., U.S.A., by artificial pollination wherein two parents were crossed which previously had been studied in the hope that they would contribute the desired characteristics. The female parent (i.e., the seed parent) was the *Caryopteris×clandonensis* 'Durio' variety (U.S. Plant Pat. No. 16,913). Such female parent sometimes bears the PINK CHABLIS designation. The male parent (i.e., pollen parent) was an unnamed *Caryopteris tangutica* plant (non-patented in the United States) which is understood to be native of China. The parentage of the new plant can be summarized as follows:

'Durio' × Unnamed
*Caryopteris × clandonensis* × *Caryopteris tangutica.*

The seeds resulting from the pollination were sown and small plants were obtained which were physically and biologically different from each other. Selective study resulted in the identification of a single plant of the new variety.

It has been found that the new *Coryopteris* plant of the present invention displays the following combination of characteristics:

(a) displays a rounded ascending growth habit with strong branching,
(b) forms large vibrant violet-blue flowers in a verticillaster arrangement, (c) displays attractive large glossy dark green foliage, and
(d) is well suited for providing attractive ornamentation in the landscape.

The new plant of the present invention can be grown to advantage to provide distinctive colorful ornamentation in parks and gardens.

The new plant can be readily distinguished from its ancestors and all other *Caryopteris* plants known to its originator. More specifically, the 'Durio' female parent displays a smaller plant size and forms pink flowers. The unnamed male parent displays leaves that are narrower and lighter green in coloration when compared to the new variety. All *Caryopteris tangutica* plants known to inventor typically form such lighter green leaves having a narrower width. The new variety can be distinguished from the 'Arthur Simmons' variety (non-patented in the United States) through the display by the new variety of sturdier branches, more uniform flowering, and the presence of large glossy dark green foliage. Also, the new variety can be readily distinguished from the 'Inoveris' variety (U.S. Plant Pat. No. 17,837) by the display by the new variety of a larger more rounded growth habit. Such 'Inoveris' variety is being marketed under the GRAND BLEU trademark.

Asexual reproduction of the new plant at West Grove, Pa., U.S.A., through the use of terminal cuttings has demonstrated that the distinctive characteristics are reliably transmitted from one generation to another. Accordingly, the new plant can be asexually reproduced in a true-to-type manner. The plant readily can be asexually reproduced via softwood and semi-hardwood cuttings.

The new plant has been named 'Novacaryfou' and will be marketed under the BLUE FOUNTAIN trademark

BRIEF DESCRIPTION OF THE PHOTOGRAPH

The accompanying photograph shows as nearly true as it is reasonably possible to make the same in a color illustration of this character, a typical specimen of the new variety. A plant at an age of approximately one year is shown while growing in the ground outdoors at West Grove, Pa., U.S.A. The plant had been asexually reproduced through the use of semi-hardwood cuttings and was growing in full sun. The photograph was obtained during September 2010.

DETAILED BOTANICAL DESCRIPTION

The following is a detailed description of the new plant of the present invention which generally was prepared while observing one-year-old plants growing in the ground outdoors in natural light during September 2011 at West Grove, Pa., U.S.A. Color terminology is in accordance with The R.H.S. Colour Chart (1995 or equivalent) of The Royal Horticultural Society, London, England, except when general color terms which are to be accorded their customary dictionary significance are used.

Type: Herbaceous perennial for garden decoration and general landscape usage.

Botanical classification: *Caryopteris hybrida.*

Plant:

- *Growth habit.*—Ascending, and generally rounded at the top.
- *Height.*—Approximately 4 feet.
- *Width.*—Approximately 4 feet.
- *Branching.*—Strong.
- *Lateral branches.*—Typically number approximately 15.
- *Branch length.*—Approximately 30 cm on average.
- *Branch diameter.*—Approximately 6 mm on average.
- *Branch texture.*—Generally smooth and covered with short pubescence.
- *Internode length.*—Commonly approximately 3.75 cm.
- *Branch color.*—Near Green Group 138B.

Foliage:

- *Arrangement.*—Decussate.
- *Length.*—Approximately 8.4 cm on average.
- *Width.*—Approximately 5.6 cm on average.
- *Shape.*—Lanceolate.
- *Apex.*—Acute.
- *Base.*—Rounded.
- *Venation.*—Pinnipalmate.
- *Margin.*—Serrate.
- *Texture.*—Bears some short pubescence.
- *Color.*—Upper surface: near Green Group 137A. Under surface: near Green Group 137C.
- *Petiole.*—Length: approximately 1.5 cm on average. Diameter: approximately 3 mm on average. Texture: bears some short pubescence. Color (upper surface): near Green Group 137D. Color (under surface): near Yellow-Green Group 145A.

Inflorescence:

- *Flowering season.*—August to first frost.
- *Arrangement.*—Verticillaster.
- *Lastingness of blooms.*—Commonly approximately two days.
- *Fragrance.*—None detected.
- *Buds shape.*—Ovoid. Length: approximately 5 mm on average. Width: approximately 3 mm on average. Color: near Violet-Blue Group 90A when tight.
- *Flowers shape.*—Zygomorphic with bilabiate petal arrangement. Diameter: approximately 5 mm on average. Depth: approximately 1 cm for total flower length. Funnel length: approximately 7 mm at opening. Texture: commonly with some short pubescence on the outside. Petal number: five with four petals being fused to form an upper lip and one larger elongated petal on the lower lip thereby forming a funnel-shaped structure. Petal length: approximately 8 mm for the four fused petals on the upper lip, and approximately 1.1 cm for the larger elongated petal on the lower lip. Petal width: approximately 7 mm on average for all petals. Petal apex: the four fused petals on the upper lip each have a aristulate apex, and the larger elongated petal on the lower lip commonly has a fringed border having a length of approximately 4 mm. Petal base: all petals are fused at the base. Petal margin: entire for four fused petals on the upper lip, and fringed for the elongated petal on the lower lip as previously indicated. Petal texture: all petals are glabrous. Petal color (inside throat): near Violet- Blue Group 90B. Petal color (outside throat): near Violet-Blue Group 90D. Stamen number: four per flower. Stamen disposition: exserted. Filament length: approximately 1 cm on average. Filament diameter: approximately 0.1 mm on average. Filament color: near Violet-Blue Group 89B. Anther shape: bi-lobed. Anther length: approximately 0.5 mm. Anther diameter: approximately 0.2 mm. Anther color: near Violet-Blue Group 98B. Pollen: no pollen detected during observations to date. Pistil number: one per flower. Pistil length: approximately 1.4 cm. Pistil disposition: erect. Style length: approximately 1.1 cm. Style diameter: approximately 0.2 mm. Style color: Violet Group 84A. Stigma shape: bifid. Stigma length: approximately 1 mm. Stigma color: Violet Group 84A. Ovary color: Yellow-Green Group 145A. Fruit/seeds: formed and fertile, and believed to be generally comparable to that of the species.
- *Sepals.*—Number: five fused to form a calyx tube. Length: approximately 5 mm. Width: approximately 3 mm. Apex: acute. Base: fused. Margin: entire. Texture: commonly bear short pubescence. Color (upper surface): when fully open Yellow-Green Group 147B overlaid with Violet Group 90A. Color (under surface): when fully open Yellow-Green Group 147B overlaid with Violet Group 90A.
- *Peduncle.*—Length: approximately 3 mm. Diameter: approximately 0.5 mm. Color: near Green Group 138C.

Development:

- *Tolerance to diseases.*—During observations to date the plant is believed to be typical of the genus.
- *Resistance to pests.*—During observations to date the plant is believed to be typical of the genus.
- *Hardiness.*—Has been observed to be hardy in U.S.D.A. Hardiness Zone Nos. 7 to 9.

Plants of the new 'Novacaryfou' variety have not been observed under all possible environmental conditions to date. Accordingly, it is possible that the phenotypic expression may vary somewhat with changes in light intensity and duration, cultural practices, and other environmental conditions.

I claim:

1. A new and distinct *Caryopteris* plant having the following combination of characteristics:

(a) displays a rounded ascending growth habit with strong branching, (b) forms large vibrant violet-blue flowers in a verticillaster arrangement, (c) displays attractive large glossy dark green foliage, and (d) is well suited for providing attractive colorful ornamentation in the landscape;

substantially as illustrated and described.

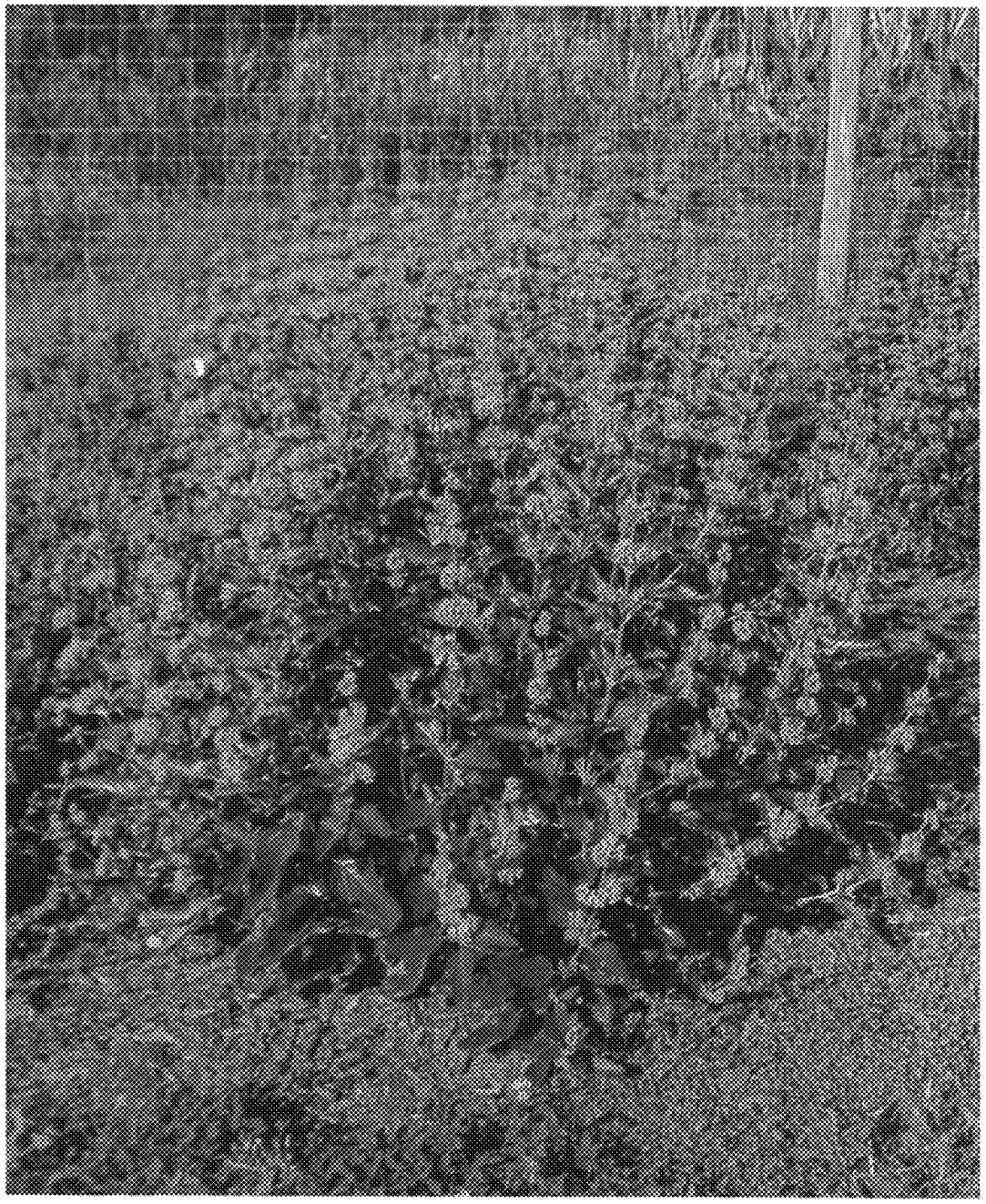

* * * * *